United States Patent [19]
Stephens

[11] 4,193,174
[45] Mar. 18, 1980

[54] LEVER AND FULCRUM CLAMPING ASSEMBLY

[75] Inventor: Thomas P. Stephens, Boxford, Mass.

[73] Assignee: Portex, Inc., Wilmington, Mass.

[21] Appl. No.: 895,405

[22] Filed: Apr. 11, 1978

[51] Int. Cl.² .............................................. A44B 21/00
[52] U.S. Cl. ............................ 24/249 R; 24/132 WL;
    24/255 SL; 251/10; 128/346
[58] Field of Search ........... 24/249 R, 248 R, 255 SL,
    24/30.5 R, 132 R, 257, 132 WL; 251/9, 10;
    128/346

[56] References Cited

U.S. PATENT DOCUMENTS

| 440,655 | 11/1890 | Sawyer | 24/248 R |
| 2,193,407 | 3/1940 | Hagen | 24/132 WL |
| 3,698,681 | 10/1972 | Lacey | 24/132 R |
| 3,896,527 | 7/1975 | Miller et al. | 24/132 R |
| 3,942,228 | 3/1976 | Buckman et al. | 251/10 |

FOREIGN PATENT DOCUMENTS 2718985  10/1977  Fed. Rep. of Germany .............. 251/9

*Primary Examiner*—Kenneth Dorner
*Attorney, Agent, or Firm*—Pollock, Vande Sande & Priddy

[57] ABSTRACT

The present invention relates to a one-piece tubular clamping assembly formed from a plastic type material and comprising a first clamping arm engageable with a flange positioned on a second clamping arm to create a unique lever and fulcrum structure capable of securing one or more concentric tubular members in place or blocking a flow path through a tubular member. The present invention further comprises a novel locking mechanism for preventing accidental disengagement of the clamping assembly.

12 Claims, 10 Drawing Figures

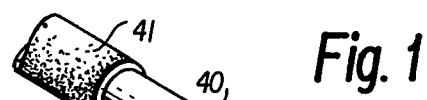
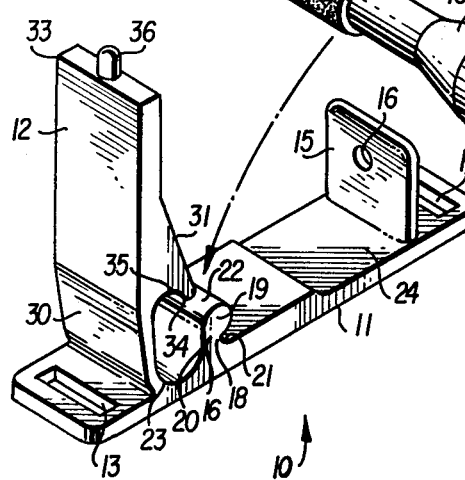
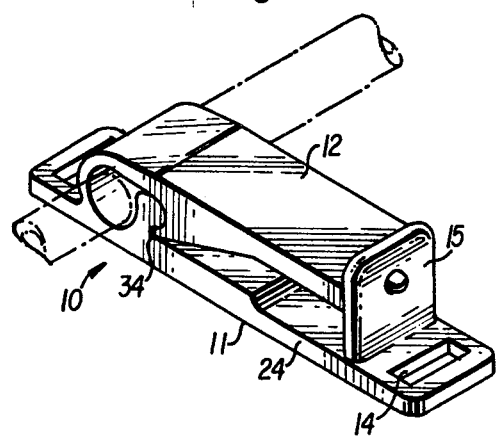
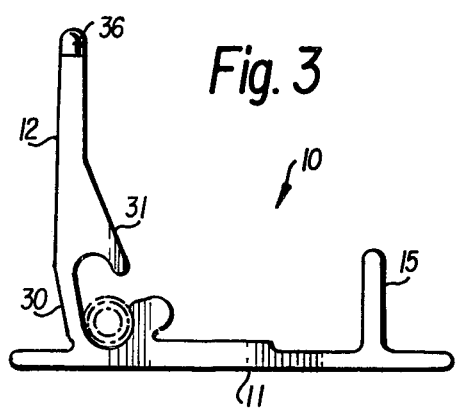
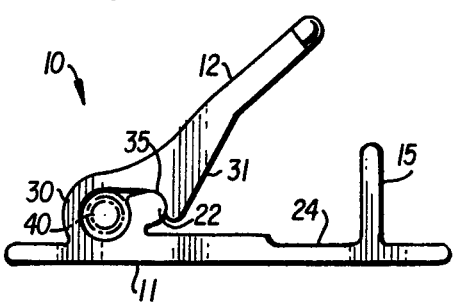
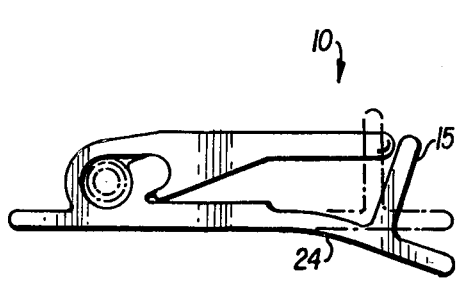
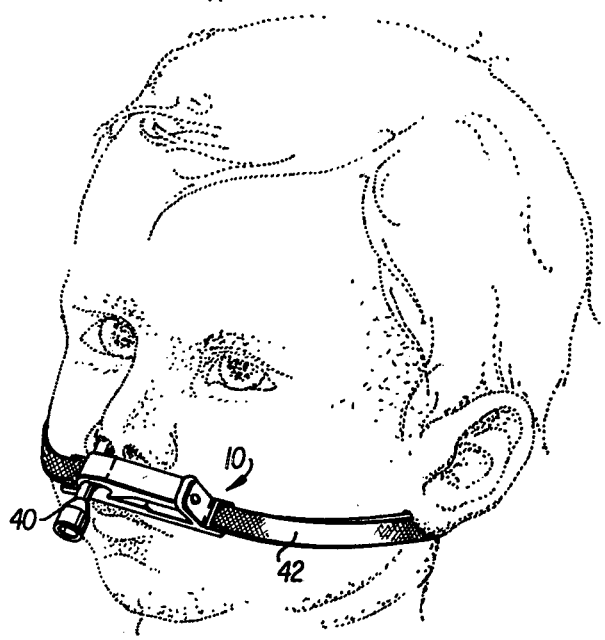

LEVER AND FULCRUM CLAMPING ASSEMBLY

BACKGROUND OF THE INVENTION

The present invention relates to a new and useful tubular clamping assembly for porviding an effective clamping force through the use of a unique lever and fulcrum structure. The present invention further includes a novel locking mechanism for preventing accidental disengagement of the clamping assembly.

Problems confronting known tubular clamping assemblies adaptable for use in the medical field include a constant clamping pressure required during the securing of a tubular member and inadvertent release of the secured clamping assembly. As an example, U.S. Pat. No. 3,629,912 issued Dec. 28, 1971 to Klopp is typical of the known prior art and suggests a clamping assembly which requires full clamping pressure to be continuously exerted during the clamping procedure, resulting in increased operator fatigue as well as increased difficulty in locking the clamping arms together. In comparison, applicant's invention employs a lever and fulcrum to develop a mechanical advantage which maintains the clamping arms in a semi-closed position with little operator pressure being required. This allows for a quick actuation as well as a much easier locking procedure.

Furthermore, the ball and socket locking mechanism of Klopp is susceptible to premature failure, in that the socket must be expanded during each engagement of the clamping assembly, resulting in the gradual deformation of the socket leading to premature disengagement of the clamping assembly.

A further example of the prior art in U.S. Pat. No. 3,942,228 issued March 9, 1976 to Buckman et al and suggesting a clamping assembly adaptable for pinching off a tubular member supported therebetween. It is further noted, that the clamping assembly in Buckman is retained in the engaged position entirely by frictional pressure. As with Klopp, the full clamping force in Buckman must be maintained during the entire actuation of the clamping assembly. Also, because a compressive clamping force must be continuously generated by the operator, the total force may not always be sufficient to ensure that fluid is continuously blocked from passing through the tubular member. Furthermore, the frictional locking mechanism in Buckman et al also has a greater susceptibility to inadvertent separation resulting from the gradual deformation of the clamping arm.

As will be discussed in detail hereinafter, an embodiment of applicant's invention overcomes the problem of an operator being required to supply a continuous clamping force, through the constant clamping force created by the unique lever and fulcrum clamping structure. An embodiment of the present invention also overcomes the problem of inadvertent clamp release by having a portion of one of the clamping arms extend through a hole formed in a flange attached to the opposite clamping arm.

While the present invention may be adaptable for use in the medical field to clamp endotracheal and similar tubular members, the present invention should not be limited to use as a medical clamp. Rather, the present invention may conveniently be used wherever a clamping assembly is considered.

OBJECTS OF THE PRESENT INVENTION

An object of the present invention is to provide a novel clamping assembly employing a lever and fulcrum structure for developing sufficient clamping force to secure concentrically positioned tubular members against relative movement.

A further object of the present invention is to provide a clamping assembly employing a lever and fulcrum structure for developing sufficient clamping force so as to selectively block a flow path through a tubular member supported within the clamping assembly.

A yet further object of the present invention is to provide a novel clamping assembly including a locking mechanism capable of preventing inadvertent disengagement of the clamping arms.

A still further object of the present invention is to provide a clamping assembly which is both inexpensive to manufacture and simple to operate.

These and other objects of the invention will become apparent from a reading of the following specification and claims, together with the accompanying drawings, wherein similar elements of each preferred embodiment are referred to and indicated by similar reference numerals with the addition of a prime (') designation.

BRIEF DESCRIPTION OF THE DRAWINGS

The present invention can be best understood with reference to the accompanying drawings, wherein:

FIG. 1 shows a perspective view of a preferred embodiment of the present invention, wherein the clamping assembly is shown in the fully open position;

FIG. 2 shows a perspective view of the preferred embodiment of FIG. 1, wherein the clamping assembly is shown in the fully closed position;

FIG. 3 shows a cross sectional view of the embodiment of FIG. 1, wherein the clamping arms are in the fully open position with a pair of concentric tubular members positioned therebetween;

FIG. 4 shows a cross section of the preferred embodiment of FIG. 3, wherein force has moved the clamping arms into a partially open position;

FIG. 5 shows a cross section similar to FIG. 2, wherein force has been exerted to move the clamping arms to the fully closed position;

FIG. 6 shows a perspective view of the preferred embodiment of FIG. 1, wherein the clamping assembly is attached to an infant's head and functions to clamp concentrically positioned endotracheal and endoconnector tubes.

DETAILED DESCRIPTION OF A PREFERRED EMBODIMENT

Figure 7:
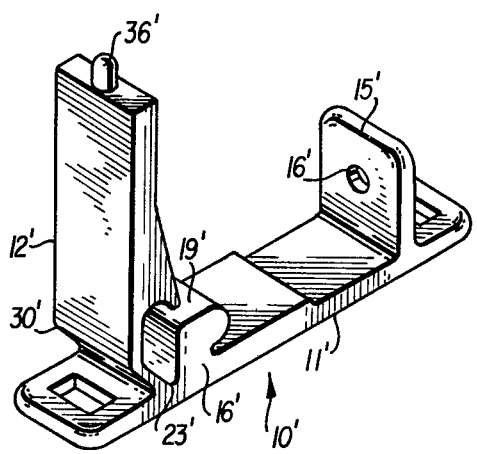
FIG. 7 shows a perspective view of a further preferred embodiment of the present invention, wherein the clamping assembly is shown in the fully open position.

Referring to the drawings, and to FIGS. 1 and 2 in particular, a clamping assembly 10 is shown in the fully opened and fully closed positions, respectively. Clamping assembly 10 comprises a pair of integrally attached, rectangular clamping arms 11 and 12.

Clamping arms 11 is formed with a pair of apertures 13 and 14 extending through opposite end portions thereof. Clamping arm 11 also includes a pair of spaced, flange members 15 and 16 extending approximately 90° from a flat surface of arm 11. Flange 15 is of a generally, rectangular shape and is positioned adjacent to aperture 14. A through aperture 17 is formed in flange member 15 and is positioned approximately two thirds of the distance from the surface of clamping arm 11 to an opposite end surface of flange 15.

Flange member 16 is of a generally, cylindrical shape and includes a recessed neck portion 18 and an enlarged end portion 19. Neck portion 18 is formed by a pair of concavely shaped surfaces 20 and 21, while end portion 19 is formed by a convexly shaped surface 22 integrally attached to surfaces 20 and 21.

A cylindrically shaped, shallow groove 23 is formed in clamping arm 11 and extends between curved surface 20 and attached clamping arm 12. As will be described in greater detail, groove 23 acts to position one or more concentric tubular members prior to actuation of clamping assembly 10. A portion of clamping member 11 is formed of a reduced cross-sectional width 24 and extends approximately ½ the distance from flange 15 toward flange 16.

Clamping arm 12 includes a first portion 30 of reduced cross-sectional width extending from groove 23 a distance approximately equal to the height of flange 15. A wedge-shaped portion 31 is attached to a side of clamping arm 12 facing flange 15 and tapers from portion 30 to a point approximately ½ the distance to a flat end surface 33 of arm 12.

Wedge-shaped portion 31 is formed with a rounded end surface 34 spaced from end portion 22 of flange 16 when clamping assembly 10 is in the fully open position, as shown in FIG. 1. Wedge 31 also includes a shallow groove 35 extending between end surface 34 and reduced cross-sectional portion 30 of clamping arm 12. Finally, a rounded pin member 36 extends from surface 33 and is centrally positioned thereon.

A pair of concentrically positioned tubular members 40 and 41 are shown in FIG. 1 as being positionable (see dotted line) between arms 11 and 12 of clamping assembly 10. For explanation purposes only, it may be considered that tubular member 40 attaches to an endoconnector, while tubular member 41 is part of a nasal endotracheal tube.

The clamping assembly comprising the present invention may be formed of a plastic such as nylon, high density polyethylene or similar material which is bendable and yet fairly rigid. The present invention may be constructed by known injection molding techniques which, in themselves, play no part in the present invention.

Operation of the preferred embodiment of FIG. 1 will be more clearly understood with regard to FIGS. 3-5. In FIG. 3, clamping assembly 10 is in the fully open position and concentric tubular members 40 and 41 have been placed within groove 23. Because clamping assembly 10 is formed of a plastic like material, clockwise movement of clamping arm 12 toward clamping arm 11 results in the bending of portion 30 of arm 12 accordingly.

Referring to FIG. 4, it is noted that the narrow portion 30 of clamping arm 12 now contacts the outer surface of tubular members 40 and 41, while groove 35 surrounds and abuts rounded end portion 22 of flange 16. When in this position, arm 12 and flange 16 act as a lever and fulcrum to create a mechanical advantage which maintains assembly 10 in the closed position and greatly reduces the remaining clockwise force necessary for locking clamping arms 11 and 12 together.

As shown in FIG. 5, portion 24 of clamping arm 11 is deformed slightly to allow arm 12 to assume the fully closed position, wherein rounded surface 34 extends between flange 16 and arm 11. The deformation of arm 11 may be accomplished either by direct contact of flange 15 with arm 12, or by the operator grasping and bending arm 11. After clamping arm 12 has attained the fully closed position, the pressure on arm 11 is released and pin 36 is allowed to extend through aperture 16, locking clamping assembly 10 against accidental release.

To disengage clamping assembly 10, the end portion 24 of clamping arm 11 is again bent slightly to release pin 36 from aperture 16. Clamping arm 12 is then rotated in the counter clockwise direction to free tubular members 40 and 41. As shown in FIG. 6, the preferred embodiment of the present invention may be used with a strap 42 which extends about an infant's head and attaches to apertures 13 and 14, respectively. The clamping assembly 10 will positively lock one or more endotracheal tubes in place, allowing fluid flow therethrough in spite of the infant's moving about or pulling on the tubes and connections.

A further preferred embodiment of the present invention is shown in FIGS. 7-10, wherein a clamping assembly 10' functions to selectively block or pinch off a flow path through a tubular member positioned within the clamping assembly.

Clamping assembly 10' differs from clamping assembly 10, discussed in the previous embodiment, in the shape of flange 16', groove 23' and portion 30' of clamping arm 12'. In the further preferred embodiment, flange 16' includes a flat surface 19' as compared to the curved surface 19. Also, groove 23' is formed with a steep incline as compared to the shallow incline of groove 23. Finally, portion 30' is actually formed by a first portion 30'A extending at an angle of approximately 60° to arm 11, and a second, integrally attached portion 30'B extending at an angle of approximately 90° to arm 11.

Each of the changes associated with clamping assembly 10' as compared to assembly 10 helps ensure that a flow path through a tubular member 40' will be completely blocked when the coupling 10' assumes the fully closed position.

Figure 8:
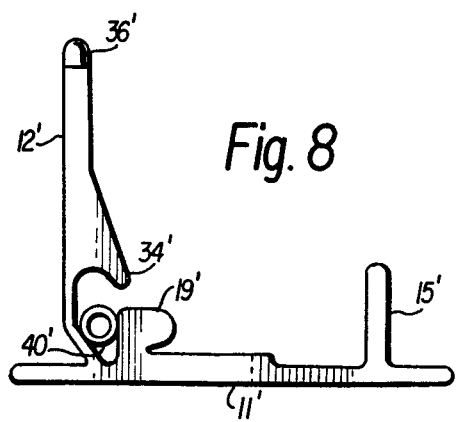
FIG. 8 shows a cross sectional view of a clamping assembly according to the embodiment of FIG. 7, wherein a tubular member is positioned between a pair of fully open clamping arms.
Figure 9:
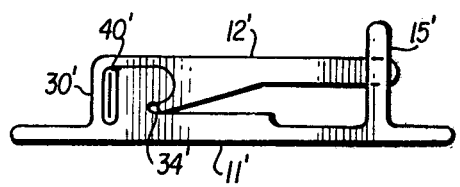
FIG. 9 shows a cross sectional view similar to FIG. 8, wherein the clamping arms are shown in the fully closed position to block flow through the tubular member supported therebetween.
Figure 10:
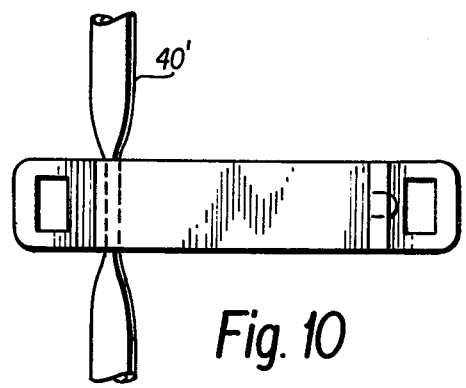
FIG. 10 shows a top view of the embodiment of FIG. 7, wherein the clamping assembly is in the fully closed position.

Operation of the further preferred embodiment of FIG. 7 will be more clearly understood with reference to FIGS. 8 and 9, respectively. In FIG. 8, the tubular member 40' has been positioned within groove 23' and arms 11' and 12' are shown in the fully open position.

Because clamping assembly 10' is also constructed of a plastic like material, clockwise force against arm 12' will deform portion 30', allowing arm 12' to move toward flange 15'. Once portion 34' of arm 12' surrounds portion 22', arm 12' and flange 16' will act as a lever and fulcrum to create a mechanical advantage which maintains assembly 10' in a closed position without additional pressure required by the operator.

Portion 24' of arm 11' is deformed to allow pin 36' to enter aperture 16' and lock the clamping assembly in the closed position. By slightly depressing portion 24' of clamping arm 11', arms 11' and 12' are unlocked and a counter clockwise pressure against arm 12' will reverse the closing procedure and completely open assembly 10'.

The present invention is not limited to use with endotracheal tubes, but may be used whenever it is desirable to hold a tube or connector in place or to completely block a flow path through a flexible connector. Furthermore, the present invention is not limited to the above described embodiments, but is limited only by the scope of the following claims.

What I claim is:

1. A clamping assembly for fixedly enclosing at least one generally tubular member, comprising:
   first and second clamping arms each having a first end portion;
   said first end portions being attached to each other to allow for the relative pivotal motion of said clamping arms;
   a flange assembly including a neck portion attached to said first clamping arm and a head portion integrally attached to said neck portion, wherein said head portion is formed with a relatively greater cross-sectional size than said neck portion;
   a generally wedge-shaped assembly extending from said second clamping arm; and
   convexly-shaped surface means formed on a portion of said flange head and engagable with complementary concavely-shaped surface means formed on a portion of said wedge-shaped assembly as said second clamping arm is pivoted toward said first clamping arm, to frictionally retain at least one tubular member positioned between said clamping arms.

2. A clamping assembly according to claim 1, wherein each of said first and second clamping arms is generally rectangular in shape.

3. A clamping assembly according to claim 1, wherein said clamping assembly is formed of a plastic-like material.

4. A clamping assembly according to claim 1, wherein said first clamping arm further includes a pair of apertures extending through opposite end portions.

5. A clamping assembly according to claim 1, wherein said first clamping arm further includes a second end portion of reduced cross-sectional width, with
   a flange extending from the second end portion in a direction generally parallel to said first connecting means, said flange being formed with an aperture extending therethrough.

6. A clamping assembly according to claim 5, wherein a knob-shaped member is attached to a second end portion of said second clamping arm and is extendable through said aperture formed in said flange to lock said clamping arms in a fully closed position.

7. A clamping assembly according to claim 1, wherein said first end portions are integrally attached to one another.

8. A clamping assembly according to claim 1, wherein said convexly-shaped surface means provides a fulcrum about which said second clamping arm is pivoted to fixedly enclose a tubular member positioned between said first and second clamping arms.

9. A clamping assembly according to claim 1, wherein a shallow groove is formed in said first clamping arm and positioned between said flange assembly and said attached second clamping arm.

10. A clamping assembly according to claim 13, wherein said first end portion of said second clamping arm extends between said groove and the concavely-shaped surface means formed on said wedge assembly,
    whereby at least one tubular member positioned within said shallow groove is clampingly enclosed without impeding a flow path through the tubular member as said flange and wedge-shaped assemblies are brought into abutting engagement.

11. A clamping assembly according to claim 1, wherein a steeply inclined groove is formed in said first clamping arm and positioned between said flange assembly and said attached second clamping arm.

12. A clamping assembly according to claim 11, wherein an L-shaped surface is formed on said flange assembly between said groove and said convexly-shaped surface means,
    and said first end portion of said second clamping arm comprises first and second attached portions inclined at an angle to one another and extending between said first clamping arm and the concavely-shaped surface means formed on said wedge-shaped assembly,
    whereby at least one tubular member positioned within said steeply inclined groove is clampingly compressed to completely block a flow path through the tubular member as said flange and wedge-shaped assemblies are brought into abutting engagement.

* * * * *